US010792183B2

(12) United States Patent
Hoffman et al.

(10) Patent No.: US 10,792,183 B2
(45) Date of Patent: Oct. 6, 2020

(54) MOBILE ARM SUPPORT (71) Applicant: Saebo, Inc., Charlotte, NC (US)

(72) Inventors: Henry B. Hoffman, Charlotte, NC (US); Freek Tonis, Enschede (NL)

(73) Assignee: Saebo, Inc., Charlotte, NC (US)

( * ) Notice: Subject to any disclaimer, the term of this patent is extended or adjusted under 35 U.S.C. 154(b) by 789 days.

(21) Appl. No.: 13/645,804

(22) Filed: Oct. 5, 2012

(65) Prior Publication Data

US 2013/0087154 A1    Apr. 11, 2013

Related U.S. Application Data

(60) Provisional application No. 61/544,053, filed on Oct. 6, 2011.

(51) Int. Cl.
*A61G 15/00*      (2006.01)
*A61F 5/37*      (2006.01)

(52) U.S. Cl.
CPC .................................. *A61F 5/3769* (2013.01)

(58) Field of Classification Search
CPC ........ A61F 5/3769; A61F 5/3761; A61F 5/37; A47C 16/00; A61G 13/12; A61G 13/1205; A61G 13/1235; A61G 13/124; A61G 13/1245; A61G 13/125; A61G 13/128; A61G 13/1255; A61G 13/1285; A61G 13/129; A61G 13/1295; A61G 15/125; A61G 15/12; A61G 13/121; A61G 13/122; A61G 13/1225; A61G 13/123; A61G 7/065; A61G 7/07; A61G 7/072; A61G 7/075; A61G 7/0755; A61G 7/1082; A61G 7/1084; A61G 7/1086; A61G 7/1088; A61G 7/109; A61G 7/1092; A61G 7/1094; A61G 7/1096; A61G 7/1098; A61B 90/60; A61B 2090/506; A61B 90/50; F16M 11/04; F16M 11/08; F16M 11/24; F16M 11/2014; F16M 11/2092; F16M 2200/063
USPC ............ 128/845; 602/32, 36, 4; 5/630, 646, 5/623, 652, 657; 248/118, 278.1
See application file for complete search history.

(56) References Cited

U.S. PATENT DOCUMENTS

| | | |
|---|---|---|
| 481,293 A | 8/1892 | Bailey et al. |
| 554,488 A | 2/1896 | Hofmeister |
| 1,706,634 A | 3/1929 | Seils |

(Continued)

FOREIGN PATENT DOCUMENTS

WO      91/14384      10/1991

*Primary Examiner* — Victoria J Hicks
(74) *Attorney, Agent, or Firm* — Nelson Mullins Riley & Scarborough LLP (57) ABSTRACT

A support assembly for a portion of a user's body includes a pivotable frame with a top elongated member, a bottom elongated member, a first side member and a second side member, the top elongated member and bottom elongated members each having first and second ends that are pivotably connected to top and bottom ends of the first side member and the second side member, respectively. A support element is operatively connected to the pivotable frame and a tensioner mechanism is adapted to adjust an amount of force required to move the support element relative to the first side member. The tension member is disposed within one of the top and the bottom elongated member and exerts a tensile force parallel to the longitudinal center axis of the one of the top and the bottom elongated member.

17 Claims, 5 Drawing Sheets

(56) References Cited

U.S. PATENT DOCUMENTS

| | | | |
|---|---|---|---|
| 2,642,250 A | 6/1953 | Kasnowich | |
| 2,950,890 A | 8/1960 | Hough, Jr. | |
| 3,124,328 A | 3/1964 | Kortsch | |
| 4,237,873 A | 12/1980 | Terry et al. | |
| 4,913,393 A | 4/1990 | Wood | |
| 4,996,977 A | 3/1991 | Tiedeken | |
| 5,074,501 A | 12/1991 | Holtta | |
| 5,135,190 A | 8/1992 | Wilson | |
| 5,281,001 A | 1/1994 | Bergsten et al. | |
| 5,360,196 A * | 11/1994 | DiGiulio | F16M 13/04 224/908 |
| 5,383,632 A | 1/1995 | Shirlin et al. | |
| 5,405,109 A | 4/1995 | Nordnes | |
| D377,125 S | 1/1997 | Adamsson | |
| 5,713,591 A | 2/1998 | Zarkhin et al. | |
| 5,718,671 A | 2/1998 | Bzoch | |
| 5,753,840 A | 5/1998 | Saboia De Albuquerque | |
| 5,895,367 A * | 4/1999 | Mautoni | 602/32 |
| 5,961,085 A * | 10/1999 | Navarro | A47C 16/00 128/878 |
| 5,975,640 A | 11/1999 | Chen | |
| 6,042,064 A | 3/2000 | Hong | |
| D438,725 S | 3/2001 | Takahashi | |
| 6,203,109 B1 | 3/2001 | Bergsten et al. | |
| 6,454,224 B1 | 9/2002 | Nogueira | |
| 6,464,183 B1 | 10/2002 | Bouhuijs | |
| 6,554,234 B2 | 4/2003 | Holdren | |
| 6,619,598 B2 | 9/2003 | De Miranda | |
| 6,619,747 B2 | 9/2003 | Ko et al. | |
| 6,663,055 B2 | 12/2003 | Boucher et al. | |
| 6,786,461 B1 | 9/2004 | Tsai et al. | |
| 6,923,505 B2 | 8/2005 | Siminovitch et al. | |
| 7,055,910 B2 | 6/2006 | Wright | |
| 7,222,826 B1 | 5/2007 | Berglund | |
| 7,461,423 B2 * | 12/2008 | Rutherford | F16M 11/04 248/118 |
| 7,562,851 B2 * | 7/2009 | Hein | F16M 11/2014 248/276.1 |
| 7,581,791 B2 | 9/2009 | Diffrient | |
| 7,823,843 B2 * | 11/2010 | Oberlaender | F16M 11/046 248/118 |
| 7,866,613 B2 | 1/2011 | Cramer | |
| 2008/0203249 A1 | 8/2008 | Priest | |
| 2009/0121111 A1 | 5/2009 | Stuijt et al. | |

* cited by examiner

MOBILE ARM SUPPORT

CLAIMS OF PRIORITY

This application claims priority to U.S. Provisional Application Ser. No. 61/544,053, filed Oct. 6, 2011, the entire disclosure of which is incorporated by reference herein.

FIELD OF THE INVENTION

The present invention relates generally to medical devices. More particularly, the present invention relates to an arm support that can be adjusted to provide varying degrees of support.

BACKGROUND OF THE INVENTION

Quite often, neurological and/or orthopedic patients exhibit poor to fair muscle strength in their upper torso, shoulders, arms, etc. As such, it is difficult to perform many functional tasks such as eating, drinking, grooming, grasping objects, etc. Additionally, these patients are often easily fatigued when performing the exercises required to strengthen the subject muscles. As such, it is known to provide devices that assist the patient by supporting a given amount of the weight of the patient's arm.

Known arm rests and support devices often include complex tension mechanisms such as, but not limited to, slings, pistons, etc., which decrease the overall versatility of the devices. More specifically, these tension mechanisms are often difficult and time consuming to both set-up and adjust with regard to the amount of support being provided. As would be expected, not only are these complex mechanisms often expensive to manufacture and maintain, they can inhibit the patient's ability to quickly and easily select a desired amount of support when, for example, transitioning from using the support during exercise (less support desired) to using it to perform fine motor action movements (more support desired), or vice versa.

Additionally, the tension mechanisms of existing arm supports are often mounted externally to a frame of the support. As such, the pistons, springs, pulleys, etc., are exposed. This can be both troublesome and dangerous in those instances where the patient may have intravenous therapy leads, heart monitor leads, etc., secured to the supported arm due to the increased risk of entanglement with the components of the tension mechanism.

The present invention recognizes and addresses considerations of prior art constructions and methods.

SUMMARY OF THE INVENTION

One embodiment of a support assembly for supporting a portion of a user's body in accordance with the present disclosure includes a pivotable frame with a top elongated member, a bottom elongated member, a first side member and a second side member, the top elongated member and the bottom elongated members each having first and second ends that are pivotably connected to top and bottom ends of the first side member and the second side member, respectively. A support element is operatively connected to the pivotable frame and adapted to receive the portion of the user's body to be supported. A tensioner mechanism is adapted to selectively adjust an amount of force required to move the support element relative to the first side member. The tension member is disposed within one of the top and the bottom elongated members and exerts a tensile force parallel to a longitudinal center axis of the one of the top and the bottom elongated member.

Another embodiment of a support assembly for supporting a portion of a user's body in accordance with the present disclosure includes a pivotable frame with a top elongated member, a bottom elongated member, a first side member and a second side member, the top elongated member and the bottom elongated members each having first and second ends that are pivotably connected to top and bottom ends of the first side member and the second side member, respectively. A support element is operatively connected to the pivotable frame and adapted to receive the portion of the user's body to be supported. A tensioner mechanism is adapted to selectively adjust an amount of force required to move the support element relative to the first side member, the tensioner mechanism including a tension member and an adjustment assembly configured to adjust an amount of force exerted on the tension member. The adjustment assembly is adapted to increase the amount of force applied to the tension member when rotated in a first direction and decrease the amount of force exerted on the tension member when rotated in an opposite second direction.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Repeat use of reference characters in the present specification and drawings is intended to represent same or analogous features or elements of the invention according to the disclosure.

DETAILED DESCRIPTION OF THE PREFERRED EMBODIMENTS

Reference will now be made in detail to presently preferred embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

Figure 1:
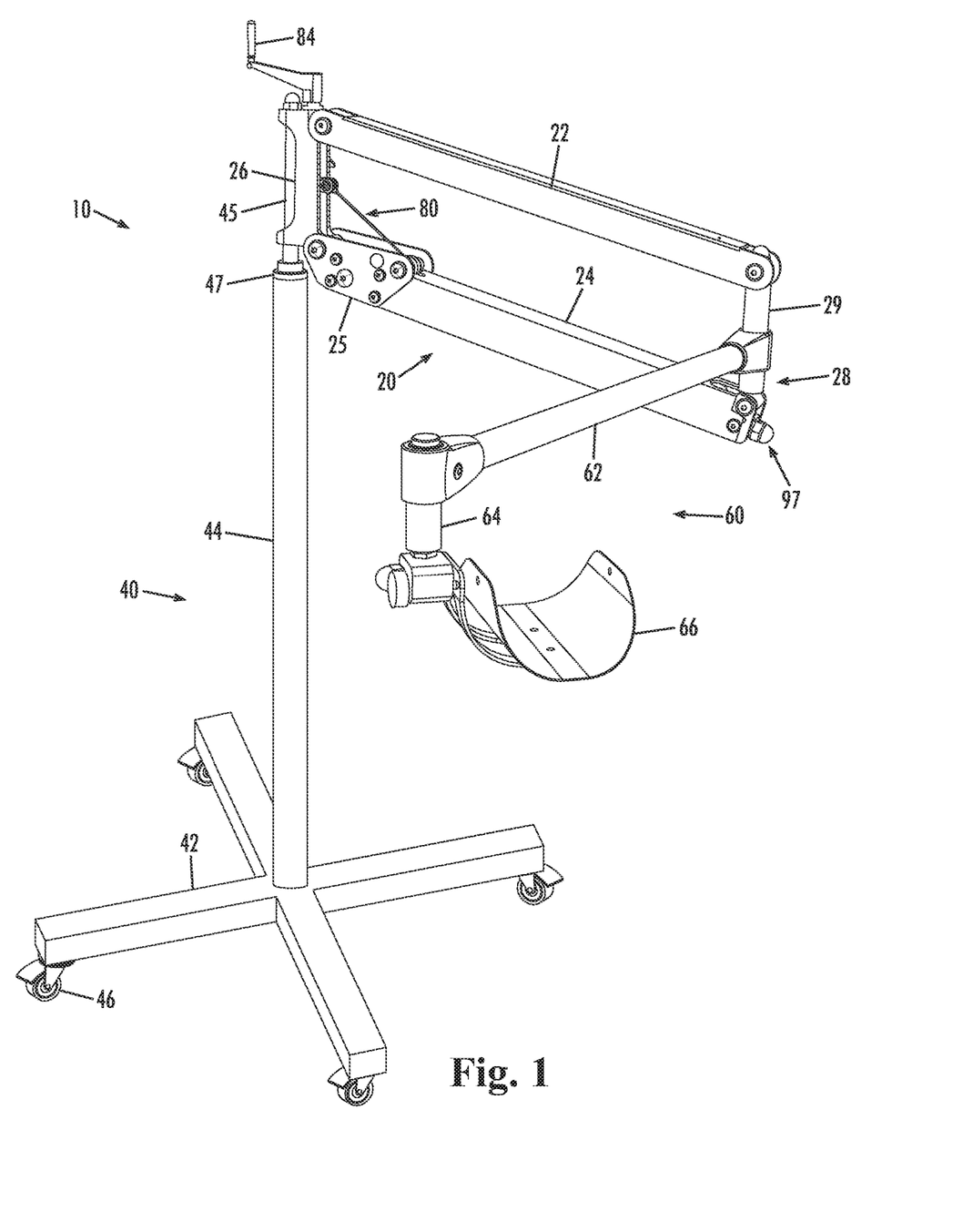
FIG. 1 is a perspective view of a mobile arm support in accordance with an embodiment of the present invention.
Figure 2:
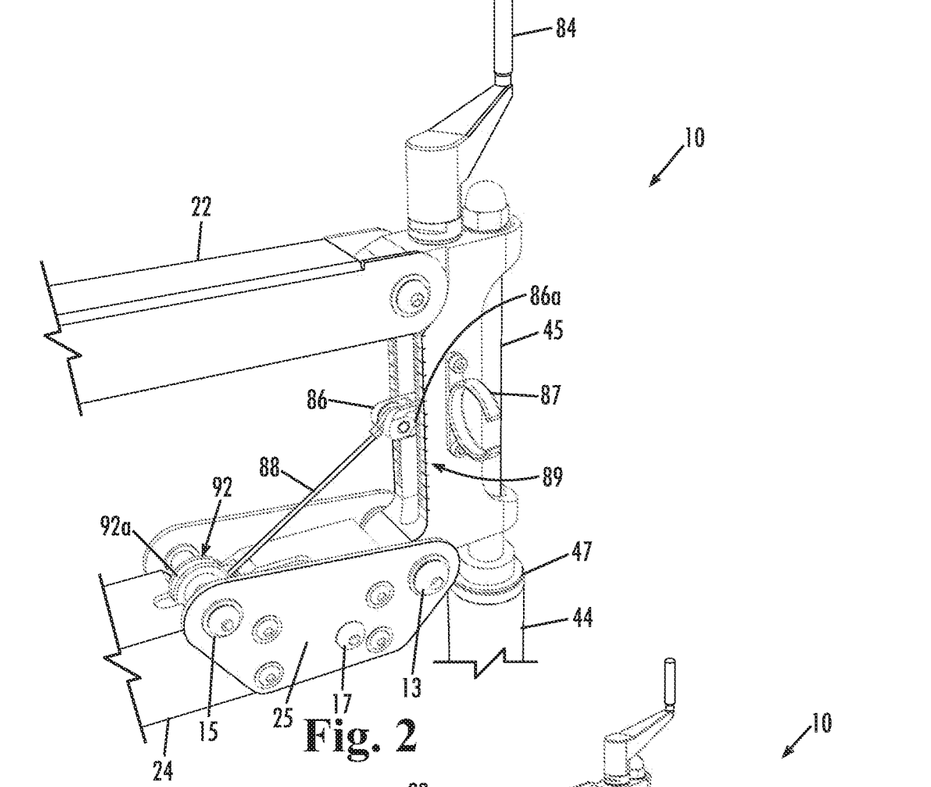
FIG. 2 is a partial perspective view of the mobile arm support shown in FIG. 1.
Figure 3:
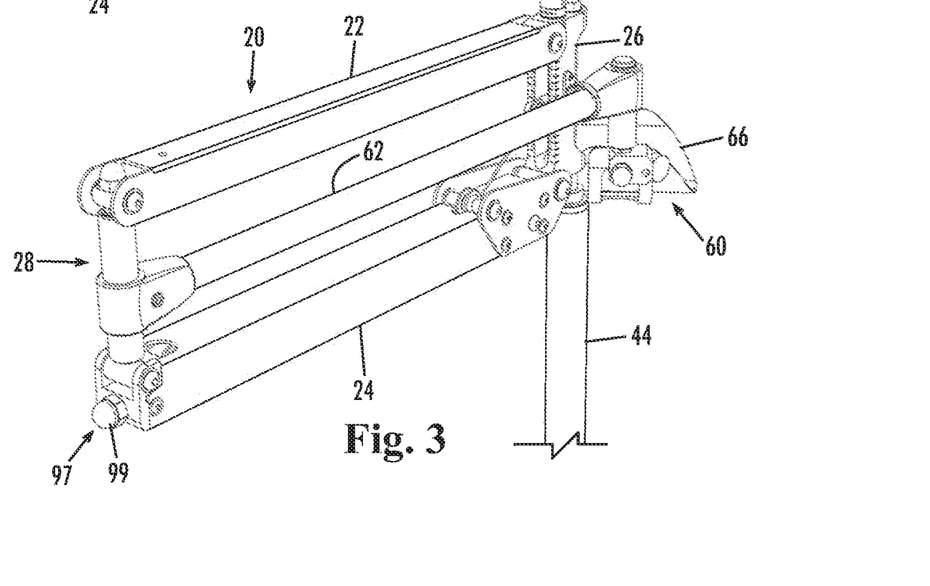
FIG. 3 is a partial perspective view of the mobile arm support shown in FIG. 1.

Referring now to FIGS. 1 through 3, an embodiment of a mobile arm support 10 in accordance with the present disclosure includes a pivotable frame 20, a support stand 40 and an arm support 60. Pivotable frame 20 includes a top elongated member 22, a bottom elongated member 24, a first side member 26 and a second side member 28. Each of top elongated member 22 and bottom elongated member 24 are pivotably mounted at their opposing ends to opposing ends of first side member 26 and second side member 28. As such, pivotable frame 20 forms a parallelogram in which second side member 28 can be moved both up and down relative to first side member 26, while at the same time remaining parallel to first side member 26.

Figure 4:
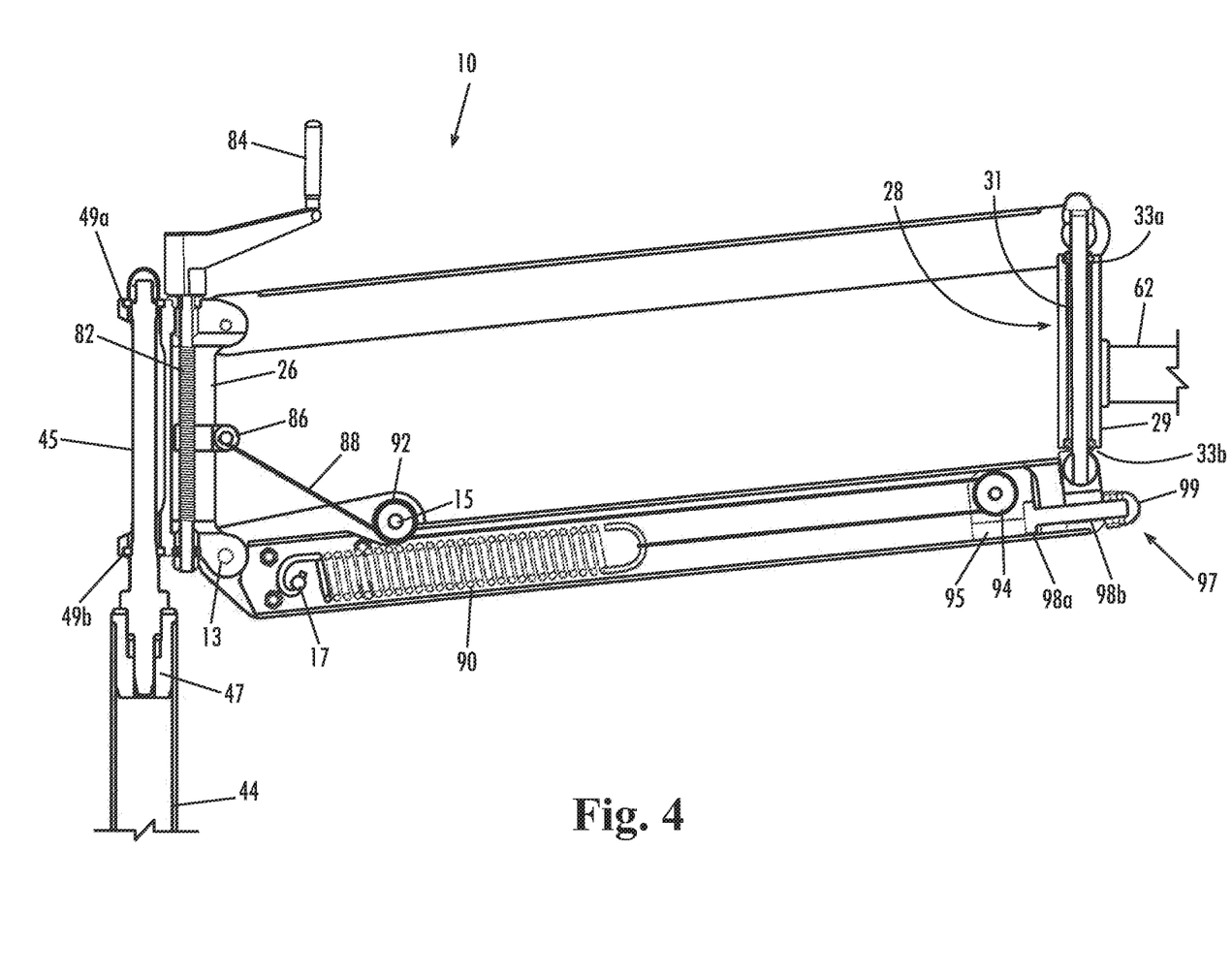
FIG. 4 is a partial, cut-way view of the mobile arm support shown in FIG. 1.

Pivotable frame 20 is mounted to a vertical support 44 of support stand 40 by first side member 26 such that pivotable frame 20 is rotatable relative to support stand 40. More specifically, as best seen in FIG. 4, first side member 26 is rotatably mounted to a support shaft 45 that is rotatably received in a bushing 47 disposed in an open top end of vertical support 44. Preferably, bushing 47 is formed of a low friction material such as, but not limited to, nylon, hard plastic, etc. Additionally, upper and lower bearings 49a and 49b are provided between first side member 26 and support shaft 45 to facilitate rotation of pivotable frame 20 relative thereto. As shown in FIG. 1, one embodiment of support stand 40 includes a horizontal base 42, from which vertical support 44 extends, with a plurality of wheels 46 to allow mobile arm support 10 to be positioned as required. Note, pivotable frame 20 can also be mounted to other articles, such as, but not limited to, a table top, a chair, a hospital bed, etc., provided the article includes a vertical support, as discussed above.

As shown, bottom elongated member 24 is pivotally attached to first side member 26 by a pair of mounting plates 25. Bottom elongated member 24 is affixed to mounting plates 25 by a plurality of threaded fasteners 27, with mounting plates 25 being pivotably mounted to first side member 26 by a first horizontal shaft 13, as best seen in FIG. 4. A second horizontal shaft 15 and a third horizontal shaft 17 are secured to mounting plates 25 and serve as supports for a first pulley 92 and a tension member 90, respectively, as discussed in greater detail below.

As best seen in FIG. 2, second side member 28 includes an outer collar 29 that is rotatably received about a shaft 31, which is pivotably mounted at its opposing ends to top elongated member 22 and bottom elongated member 24. Upper and lower bearings 33a and 33b are disposed between the upper and lower ends of outer collar 29, respectively, and shaft 31 to facilitate rotation of the collar relative to the shaft. Alternatively, upper and lower bushings constructed of a low friction material, such as, but not limited to, nylon, hard plastics, etc., may be used in place of the bearings.

As best seen in FIG. 1, arm support 60 includes a horizontal member 62, a first vertical member 64 and a cradle 66. Horizontal member 62 is mounted to second side member 28 of pivotable frame 20 at a first end and includes first vertical member 64 rotatably mounted at its second end. More specifically, as best seen in FIG. 4, the first end of horizontal member 62 is mounted to collar 29 of second side member 28 at its first end. Cradle 66 is rotatably mounted to first vertical member 64. In the embodiment shown, cradle 66 includes a frame and padding that are conformed to receive the underside of a user's forearm. Alternate embodiments include various configurations for cradle 66. Cradle 66 can be malleable so it can be shaped to the user's forearm. It may also include straps, such as hook and loop type straps, attached to the cradle for securing the user's arm to the support. Referring additionally to FIGS. 2 and 3, arm support 60 can be secured in a stowed position by, in the preferred embodiment shown, a C-clip 87 that is mounted to first side member 26. The opposed arms of C-clip 87 are urged outwardly by the outer surface of horizontal member 62 so it is received therebetween and retained thereby. Other embodiments may include magnets, hook and look-type fasteners, etc., to retain arm support 60 in the stowed position.

As best seen in FIG. 3, mobile arm support 10 further includes a tensioner mechanism 80. Tensioner mechanism 80 includes a threaded shaft 82, an adjustment handle 84, a carrier 86, a cable 88 and a tension member 90. Threaded shaft 82 is rotatably received within first side member 26 of pivotable frame 20 and adjustment handle 84 is connected to its top end such that adjustment handle 84 may be used to rotate threaded shaft 82. Carrier 86 is free to travel along the length of threaded shaft 82 as adjustment handle 84 is rotated in either the clockwise or counter-clockwise directions. Carrier 86 includes a pointer 86a that moves along a graduated scale 89 provided on first side member 26. Pointer 86a and scale 89 allow a user to readily determine the amount of support being provided while adjusting the tension mechanism. A first end 88a of cable 88 is secured to carrier 86 and a second end 88b of cable 88 is secured to coil spring 90 which, in turn, is secured to mounting plates 25 of bottom elongated member 24 by third horizontal shaft 17. In the preferred embodiment shown, tension member 90 comprises a coil spring. Note, however, alternate embodiments may include elastic bands, or other similar elements, to provide the desired amount of tension.

In the preferred embodiment shown, a first pulley 92 and a second pulley 94 are used to direct the travel of cable 88 between carrier 86 and coil spring 90. As previously noted, first pulley 92 is rotatably supported on second support shaft 15, which is supported by mounting plates 25. Second pulley 94 is rotatably supported by a frame 95 at the opposite end of bottom elongated member 24. As shown in FIG. 4, frame 95 is slidably positioned in bottom elongated member 24 by an adjustment assembly 97. Adjustment assembly 97 includes a threaded bolt 98 and correspondingly threaded nut 99. A head 98a of threaded bolt 98 is affixed to frame 95 and a threaded stem 98b passes through an aperture in the second end of bottom elongated member 24. Threaded nut 99 is received on threaded stem 98b so that rotation of threaded nut 99 causes bolt 98 and, therefore, frame 95 to move longitudinally along the center axis of bottom elongated member 24. Movement of second pulley 94 toward the second end of bottom elongated member 24 increases tension exerted on cable 88, whereas motion toward the first end of bottom elongated member 24 reduces tension exerted on cable 88.

Cable 88 is received in an annular groove 92a of first pulley 92 so that cable 88 enters bottom elongated member 24. A first portion of cable 88 extends from first pulley 92 almost the entire length of bottom elongated member 24 toward to second pulley 94 at its second end. A second portion of cable is redirected back toward the first end of bottom elongated member 24 by second pulley 94, where it is secured to an end of the tension member, coil spring 90. As best seen in FIG. 4, in this construction both the first and second portions of cable are parallel to each other and there is the advantage that the entire coil spring 90, and practically the entire cable 88, are housed within bottom elongated member 24.

Figure 5A:
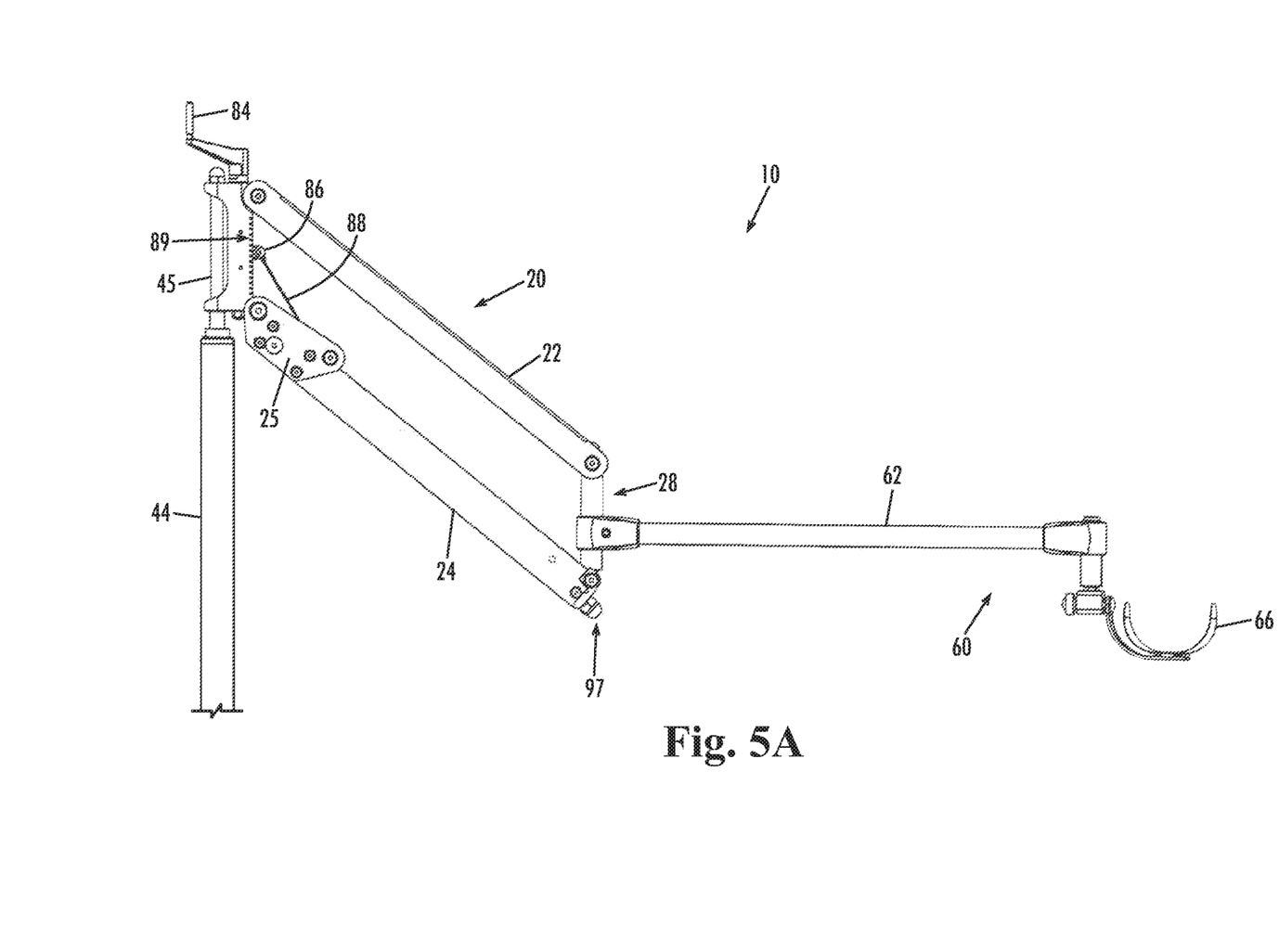
FIG. 5A is a side view of the mobile arm support shown in FIG. 1, with the arm support in a lowered position.
Figure 5B:
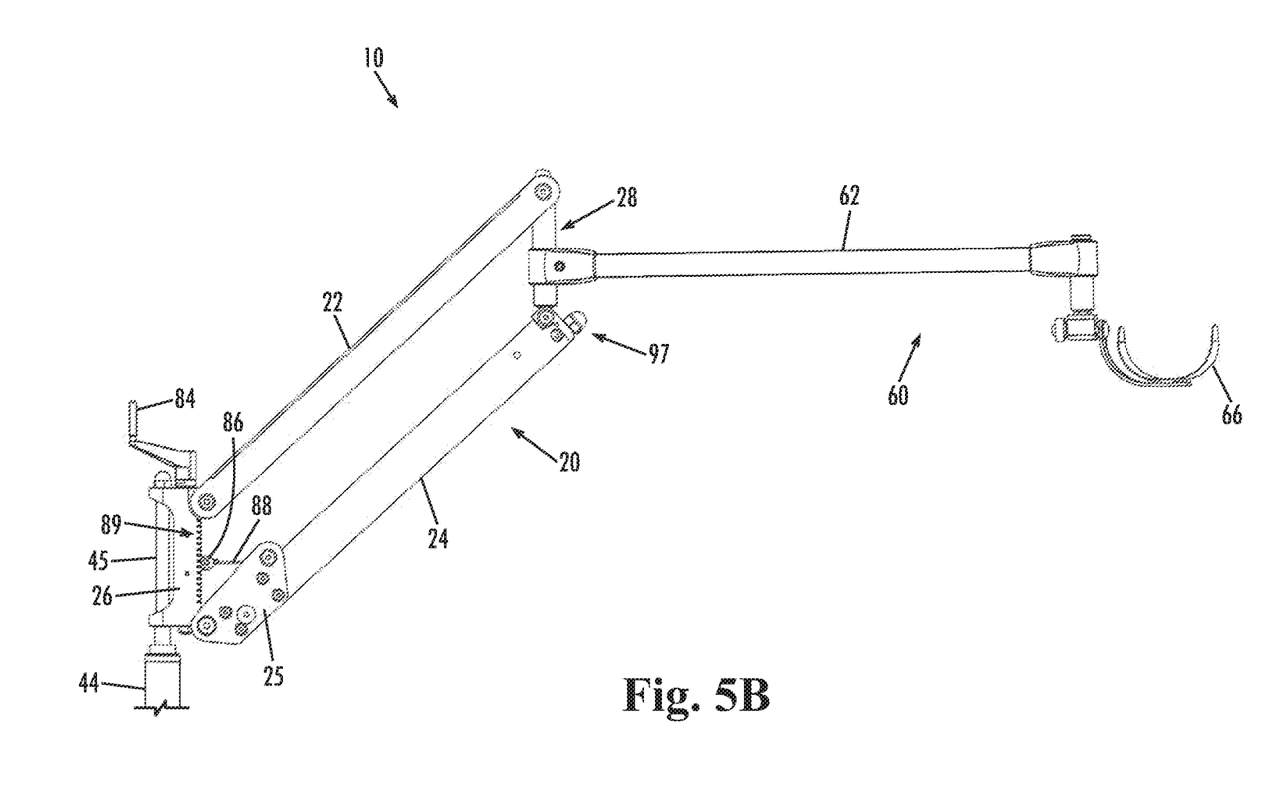
FIG. 5B is a side view of the mobile arm support shown in FIG. 1, with the arm support in a raised position.

Rotation of handle 84 in a first direction (as shown, clockwise (CW) when viewed from above) causes carrier 86 to travel upwardly along threaded shaft 82, thereby increasing the amount of force exerted on coil spring 90 by cable 88. As such, pivotable frame 20 is able to support a greater amount of weight in cradle 66 of arm support 60 prior to second side member 28, and therefore arm support 60, moving downwardly. As such, increased effort on the user's part is required to move their arm downwardly. Conversely, rotation of handle 84 in an opposite direction (as shown, counter-clockwise (CCW) when viewed from above) causes carrier 86 to move downwardly along threaded shaft 82, thereby releasing the amount of force exerted on coil spring 90 by cable 88. As such, second side member 28 of pivotable frame 20, and therefore arm support 60, is able to move downwardly although reduced amounts of weight are being supported in cradle 66 of arm support 60. FIGS. 5A and 5B show arm support 60 in its lowered and raised positions, respectively, with support being provided to the user's arm across the entire range of motion.

While one or more preferred embodiments of the invention are described above, it should be appreciated by those skilled in the art that various modifications and variations can be made in the present invention without departing from the scope and spirit thereof. It is intended that the present invention cover such modifications and variations as come within the scope and spirit of the appended claims and their equivalents.

What is claimed is:

1. A support assembly for supporting a portion of a user's body, comprising:
   a pivotable frame including a top elongated member, a bottom elongated member, a first side member and a second side member, the top elongated member and the bottom elongated member each having first and second ends that are pivotably connected to respective top and bottom ends of the first side member and the second side member;
   a support element operatively connected to the pivotable frame, the support element being adapted to receive the portion of the user's body;
   a tensioner mechanism including a tension member, the tensioner mechanism being adapted to selectively adjust an amount of force required to move the support element relative to the first side member;
   an adjustment assembly configured to adjust an amount of force exerted on the tension member, the adjustment assembly including a first pulley affixed to the first end of the bottom elongated member, a second pulley affixed to the second end of the bottom elongated member, and a cable having a first end and a second end, wherein the second end of the cable is affixed to the tension member, the cable is received on both the first pulley and the second pulley, and a first portion of the cable that extends between the first pulley and the second pulley, and a second portion of the cable that extends between the second pulley and the tension member are parallel to each other and disposed entirely within the bottom elongated member; and
   a support stand including a vertical support shaft, the first side member of the pivotable frame being rotatably mounted to the vertical support shaft so that a longitudinal center axis of the vertical support shaft is parallel to a longitudinal center axis of the first side member,
   wherein the tension member is affixed to and disposed within bottom elongated member.

2. The support assembly of claim 1, wherein a first end of the tension member is secured to the bottom elongated member and a second end of the cable is secured to a second end of the tension member.

3. The support assembly of claim 2, wherein the adjustment assembly further comprises a carrier that is movable relative the first side member in a direction parallel to the longitudinal center axis of the first side member, and the first end of the cable is secured to the carrier.

4. The support assembly of claim 3, wherein the adjustment assembly further comprises a threaded shaft, and the carrier farther comprises a bore that is correspondingly threaded so that the carrier is selectively movable along the threaded shaft upon rotation of the threaded shaft.

5. The support assembly of claim 4, wherein the threaded shaft is rotatably supported by the first side member, and the adjustment assembly further comprises a handle non-rotatably secured to an end of the threaded shaft.

6. The support assembly of claim 2, wherein the tension member further comprises a coil spring.

7. The support assembly of claim 2, wherein the second pulley is disposed within the bottom elongated member adjacent its second end so that force exerted on the tension member by the cable is exerted in a direction parallel to the longitudinal center axis of the bottom elongated member.

8. The support assembly of claim 1, wherein the support element is rotatably connected to the second side member of the pivotable frame.

9. The support assembly of claim 8, wherein the support element is adapted to receive a forearm of the user.

10. The support assembly of claim 1, wherein the support stand further comprises a base from which the vertical support shaft extends, the base being horizontal to a support surface on which the base rests and the vertical support shaft being perpendicular to the support surface.

11. A support assembly for supporting a portion of a user's body, comprising:
    a pivotable frame including a top elongated member, a bottom elongated member, a first side member and a second side member, the top elongated member and the bottom elongated member each having first and second ends that are pivotably connected to respective top and bottom ends of the first side member and the second side member;
    a support element operatively connected to the pivotable frame, the support element being adapted to receive the portion of the user's body;
    a tensioner mechanism including a tension member disposed in the bottom elongated member, the tensioner mechanism being adapted to selectively adjust an amount of force required to move the support element relative to the first side member; and
    an adjustment assembly configured to adjust an amount of force exerted on the tension member, the adjustment assembly including a first pulley affixed to the first end of the bottom elongated member, a second pulley affixed to the second end of the bottom elongated member, and a cable having a first end and a second end, wherein the second end of the cable is affixed to the tension member, the cable is received on both the first pulley and the second pulley, and a first portion of the cable that extends between the first pulley and the second pulley, and a second portion of the cable that extends between the second pulley and the tension member are parallel to each other and disposed entirely within the one of the top and bottom elongated member.

12. The support assembly of claim 11, wherein a first end of the tension member is secured to the bottom elongated member and a second end of the cable is secured to a second end of the tension member.

13. The support assembly of claim 12, wherein the tension member further comprises a coil spring.

14. The support assembly of claim 12, wherein the adjustment assembly further comprises a threaded shaft and a carrier having a bore that is correspondingly threaded to the threaded shaft so that the carrier is selectively movable along the threaded shaft upon rotation of the threaded shaft.

15. The support assembly of claim 11, wherein the support element is rotatably connected to the second side member of the pivotable frame.

16. The support assembly of claim 15, wherein the support element is adapted to receive a forearm of the user.

17. The support assembly of claim 11, further comprising:
a support stand including a vertical support shaft, the first side member of the pivotable frame being rotatably mounted to the vertical support shaft so that a longitudinal center axis of the vertical support shaft is parallel to a longitudinal center axis of the first side member,
wherein the support stand further comprises a base from which vertical support shaft extends, the base being horizontal to a support surface on which the base rests and the vertical support shaft being perpendicular to the support surface.

* * * * *